United States Patent [19]

Doebert et al.

[11] Patent Number: 4,811,372

[45] Date of Patent: Mar. 7, 1989

[54] DENTAL X-RAY DIAGNOSTIC INSTALLATION FOR PRODUCING PANORAMIC TOMOGRAMS OF THE JAW OF A PATIENT

[75] Inventors: Michael Doebert, Lorsch; Werner Guenther, Bensheim; Erich Heubeck, Bensheim; Manfred Muether, Bensheim; Dieter Molitor, Buerstadt, all of Fed. Rep. of Germany

[73] Assignee: Siemens Aktiengesellschaft, Berlin and Munich, Fed. Rep. of Germany

[21] Appl. No.: 942,747

[22] Filed: Dec. 17, 1986

[30] Foreign Application Priority Data

Dec. 20, 1985 [DE] Fed. Rep. of Germany ....... 3545436

[51] Int. Cl.⁴ .......................... A61B 6/14; G03B 41/16
[52] U.S. Cl. ......................................... 378/39; 378/38
[58] Field of Search ...................... 378/38, 39, 40, 191, 378/168–170

[56] References Cited

U.S. PATENT DOCUMENTS

| | | |
|---|---|---|
| 2,434,827 | 1/1948 | Akers . |
| 3,908,126 | 9/1975 | Hudson et al. . |
| 4,495,632 | 1/1985 | Nakano ................................. 378/38 |
| 4,683,581 | 7/1987 | Tammisalo et al. ................... 378/38 |

FOREIGN PATENT DOCUMENTS

| | | |
|---|---|---|
| 472413 | 3/1929 | Fed. Rep. of Germany . |
| 2461441 | 7/1975 | Fed. Rep. of Germany . |
| 3125243 | 4/1982 | Fed. Rep. of Germany . |
| 0204676 | 12/1986 | Fed. Rep. of Germany ........ 378/38 |
| 1195082 | 11/1959 | France . |

OTHER PUBLICATIONS

Siemens brochure entitled "Orthopantomograph 10, M–D 80/1361; WS 08832".
European Search Report.

Primary Examiner—Craig E. Church
Assistant Examiner—Joseph A. Hynds
Attorney, Agent, or Firm—Hill, Van Santen, Steadman & Simpson

[57] ABSTRACT

In order to provide a dental X-ray diagnostic installation for producing panoramic tomograms of the jaw of the patient and to achieve a simple structure with improved image quality, the apparatus includes an adjustment mechanism for the carrier of the radiation source and the film cassette holder to be adjusted in an orbital curve corresponding to the dental arch of the patient. The adjustment arrangement includes first adjustment parts with which the carrier can be rotated around a first vertical axis, and second adjustment elements for moving or swivelling the first axis in an arch transverse relative to the symmetry axis of the subject during the rotary motion. The swivel radius and the amount of excursion of this swivel motion are selected so that the perpendicular transillumination direction through the subject gives a constant distance between the subject and the film during the motion of the rotary unit. To accomplish this, the invention includes two separate embodiments with various modifications.

21 Claims, 10 Drawing Sheets

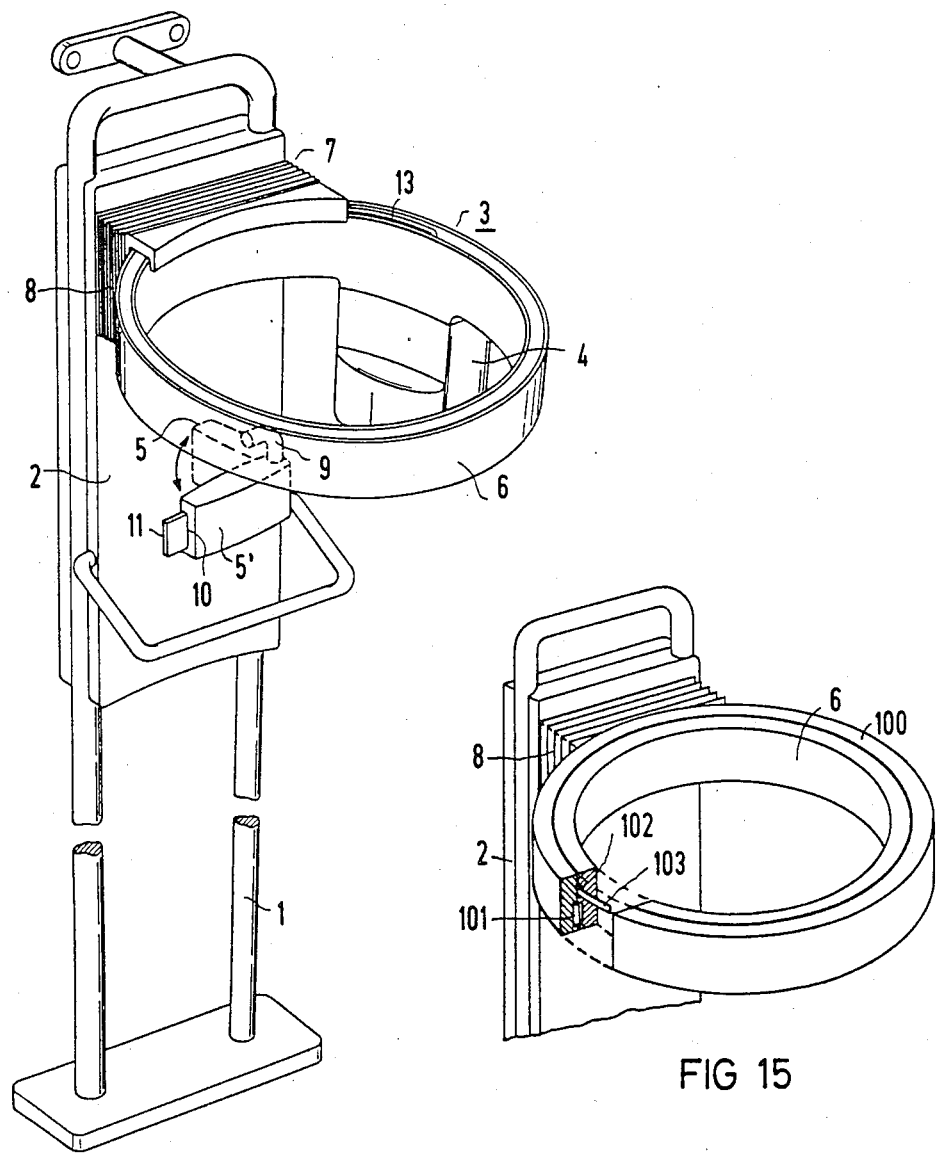
FIG 1
FIG 15
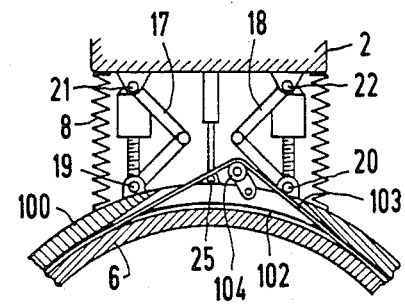
FIG 16

DENTAL X-RAY DIAGNOSTIC INSTALLATION FOR PRODUCING PANORAMIC TOMOGRAMS OF THE JAW OF A PATIENT

BACKGROUND OF THE INVENTION

The invention relates to a dental X-ray diagnostic installation for producing panoramic tomograms of the jaw of a patient. The apparatus contains a rotary unit arranged on a carriage of a stand comprising a carrier which rotates on an axis, a radiation source and a film cassette are mounted on the carrier diametrically relative to the axis with the cassette being adjustably held so that the rays coming from the radiation source impinge on the film cassette essentially perpendicular. The apparatus also includes an adjustment mechanisms with which the carrier can be adjusted in an orbit curve corresponding to a dental arch of the patient.

A known apparatus of the dental X-ray diagnostic device is a ORTHOPANTOMOGRAPH 10 which is disclosed in a brochure entitled "ORTHOPANTOMOGRAPH 10, M-D 80/1361; WS 08832". In this known device, the rotary unit contains a horizontally carrying beam whose one end accepts the radiation source and the other end accepts the film cassette holder coupled to a special mechanism so that the film cassette is stationarily inserted in the film cassette holder without any adjustments. The mechanism is thereby designed so that the film cassette holder is adjusted relative to the radiation source with a definite speed which is synchronized with the running speed of the radiation source in the course of the rotational movement of the carrier around the patient head.

The adjustment mechanism that is required in order to adjust the rotary unit in the orbital curve corresponding to the dental arch is comparatively complicated and is relatively involved in terms of its mechanical design. This is particularly true in order to achieve the required matching of the motion sequences of the rotary unit on the one hand and of the film cassette mount on the other hand.

SUMMARY OF THE INVENTION

The object of the present invention is to provide an X-ray diagnostic installation to achieve an optimum or compromise between optimally perpendicular transillumination of the subject and a high degree of avoidance of shadow formation. A perpendicular transillumination of the subject is necessary in order to achieve a superimposition-free imaging of the teeth at every location of the jaw arch. A shadow formation, which essentially occurs in that the transillumination direction does not proceed horizontally but proceeds at a slight angle or inclination from below or above, should be avoided insofar as possible in order to obtain the clearest possible exposure of the subject and, thus, an improvement of the image quality.

To accomplish this goal, the invention is directed to improvement in a dental diagnostic installation or apparatus for producing panoramic tomograms of the jaw of a patient, said installation containing a rotary unit arranged on a carriage of a stand, said rotary unit comprising a carrier rotatable on a first vertical axis, a radiation source being mounted on the carrier, a holder for a film cassette being adjustably mounted on the carrier diametric to said source so that the rays coming from the radiation source impinge on the film cassette essentially perpendicular. The unit further includes an adjustment mechanism with which the carrier is adjustable in an orbit curve corresponding to the dental arch. The improvements are that the adjustment mechanism contains first adjustment means for rotating the carrier around the first vertical axis and second adjustment means for swivelling the carrier around a swivel axis offset from the first axis by a swivel radius and transverse excursion relative to a symmetry axis of the subject during the rotational movement around the first axis whereby the swivel radius and the excursion of the swivel motion are selected so that the perpendicular transillumination direction through said subject is always provided in the movement of the rotary unit to provide a constant distance between the subject and film and in that further the film cassette is mounted adjustable relative to the radiation source.

The invention as recited hereinabove is based on the object of achieving an improvement over a known apparatus of this type, namely both in view of mechanism to be established in order to make the apparatus more compact and less costly as well as in view of the image quality. This ultimately means that as perpendicularly transillumination direction as possible is to be achieved at every location of the jaw arch and, thus, shadow formations are to be reduced to a minimum.

A significant feature of the invention is that the carrier, during its self-rotation, additionally executes a swivel motion at right angles relative to the axis of symmetry of the subject, so that the swivel radius and excursion are selected so that a transillumination direction given constant magnification, for example, given nearly constant distance between the subject and the film is always established. An optimum transillumination direction with optimum course of path length can be achieved with these measures, so that a good imaging is established, especially in the region of the front teeth.

Two embodiments, each having various modifications, shall be set forth hereinbelow. In one embodiment, the boom with the cross-girder required in the known apparatus is eliminated, as is the involved adjustment mechanism in order to achieve the synchronous motion sequence of the rotary unit and film cassette holder. The sequence curve becomes comparatively simple. It is composed first of the rotary motion which the rotary ring executes around its center axis and second of a transverse motion which the rotary ring executes by swivelling around a swivel axis arranged at the bearing point connection to the carriage. Dependent on whether only exposures in one slice position, for example, what is referred to as a standard exposure, or whether over and above the additional exposures in other slice positions, for example what is referred to as sinus exposures or exposures of the temporomaxillary joints are to be produced, the adjustment means can be fashioned and arranged so that the spacing in the rotary ring relative to the carriage is also varied.

In the second embodiment, the above advantages are likewise achieved, however, the external structure comprises a horizontal boom and a transverse carrier on whose end the radiation source and on whose other end the film cassette holder are arranged corresponding to the known designs. The adjustment mechanism, however, is significantly simpler. The pivot axis or bearing for the carrier of the film cassette holder and the source of radiation are located on a swivel plate, which is seated at a pivot point situated on the axis of symmetry of the patient. The pivot axis or bearing is moved on a circular orbit which proceeds transversely relative to the axis of symmetry of the subject and whose center line lies on the extension of the symmetrical axis of the subject. Advantageously, the swivel axis is adjustable in the direction of the symmetry axis. Not only can the most optimum transillumination directions thereby be achieved, but so can relative uniform path lengths or layer thicknesses. The adjustment of the longitudinal direction occurs during the rotation and can be optionally controlled via a mechanical curve or cam or via a separate electrical drive. A change of the slice position can be achieved in that the pin presses against the cam and this pin is not rigidly mounted on a carrier connected to the base plate, but on a carrier that executes an additional transverse motion relative to the axis of symmetry.

Additional advantages will be readily apparent from the following description, drawings and claims.

BRIEF DESCRIPTION OF THE DRAWINGS

FIG. 1 is a perspective view schematically illustrating a first embodiment of an apparatus according to the present invention;

FIG. 15 is a partial perspective view similar to FIG. 1 showing another modification of the ring arrangement in accordance with the present invention; and FIG. 16 is a partial cross-sectional view showing the modification for FIG. 15 with the means for adjustment.

DESCRIPTION OF THE PREFERRED EMBODIMENTS

Figure 2:
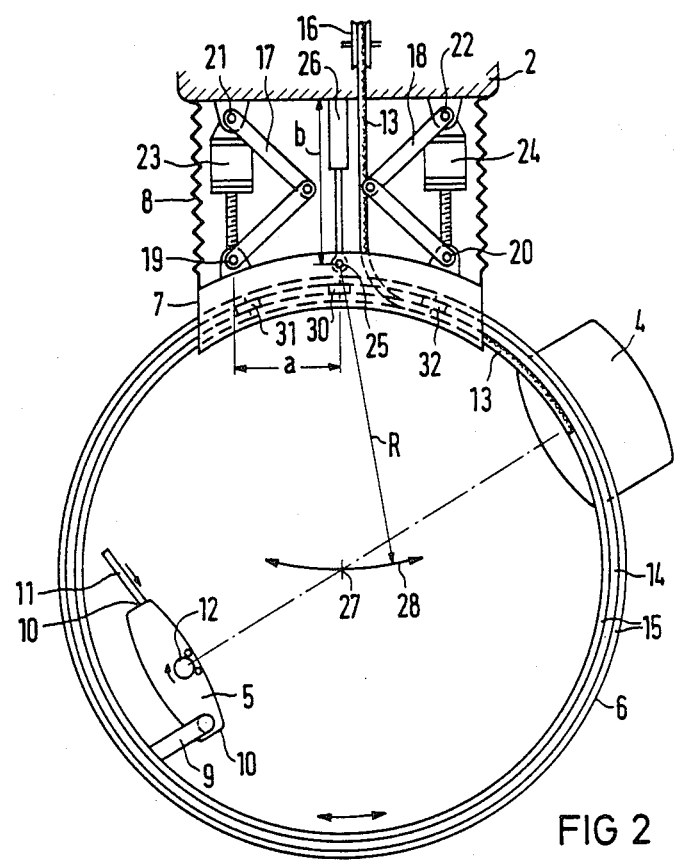
FIG. 2 is a plan top view with portions broken away for purposes of illustration of the rotary ring of the first embodiment.

The principals of the present invention are particularly useful when incorporated into a X-ray diagnostic installation illustrated in FIG. 1. Installation or apparatus of FIG. 1 includes a stand 1 constructed of two vertical pipe risers, and a carriage 2, which is arranged on the stand 1 and is adjustable in a vertical direction. A rotary unit is generally indicated at 3 and is mounted on the carriate 2. The rotary unit 3 includes a rotary ring 6 which has mounted thereon an X-ray source 4 and, diametrically opposite to the source 4, a film cassette holder 5. The ring 6 is mounted by a bearing part 7 for rotation on the carriage 2 and can be moved in a swivel fashion. The adjustment mechanism between the carriage 2 and the ring 6 is covered by an accordion bellows 8 in FIG. 1.

As best illustrated in FIG. 2, the radiation source 4 is rigidly arranged on the rotary ring 6, and the film cassette holder 5, by contrast, is held for pivotal movement around the vertical axle bearing which is carried on the free end of a carrying arm 9 which is bent at right angles and is secured to the ring 6. For better patient positioning or, respectively, for special exposures, such as CEPH exposures, the film cassette can thus be brought out of its usual position shown in broken lines in FIG. 1 into a non-used position 5' as shown in solid lines. The film cassette holder 5 contains a slot 10 on each of its two end faces. A film cassette 11 is introduced via one slot and is withdrawn through the other slot after the film exposure. Within the film cassette holder 5, the film, as schematically shown in FIG. 2 is conducted past an exposure location at which the central rays impinge by means of a suitable transport roller 12, which will move it at the defined speed.

Electrical feed of the radiation source 4 occurs by means of a power line or cable 13 which is guided up to the bearing part 7 in one of two annular channels 15 which are provided on both edges of the ring 6 on opposite sides of a running rail 14, which is provided on each side or edge of the ring 6. The cable 13 is guided by suitable pulleys or rollers 16 in the carriage 2 adjacent the bearing part 7.

As illustrated in FIG. 2, the ring 6 and the bearing part 7 are mounted on the carriage 2 by two pairs of scissor arms 17 and 18 which are connected by pivot connections 19 and 20, respectively, to the part 7 and are connected to the carriage by pivot points or articulations 21 and 22. A pair of spindle drives 23 and 24 are provided and extend between the pivot connections with the drive 23 extending between the pivot connections 19 and 21 and the drive 24 extending between the connections 20 and 22. These drives 23 and 24 are capable of being individually driven by a control means (not shown).

Figure 14:
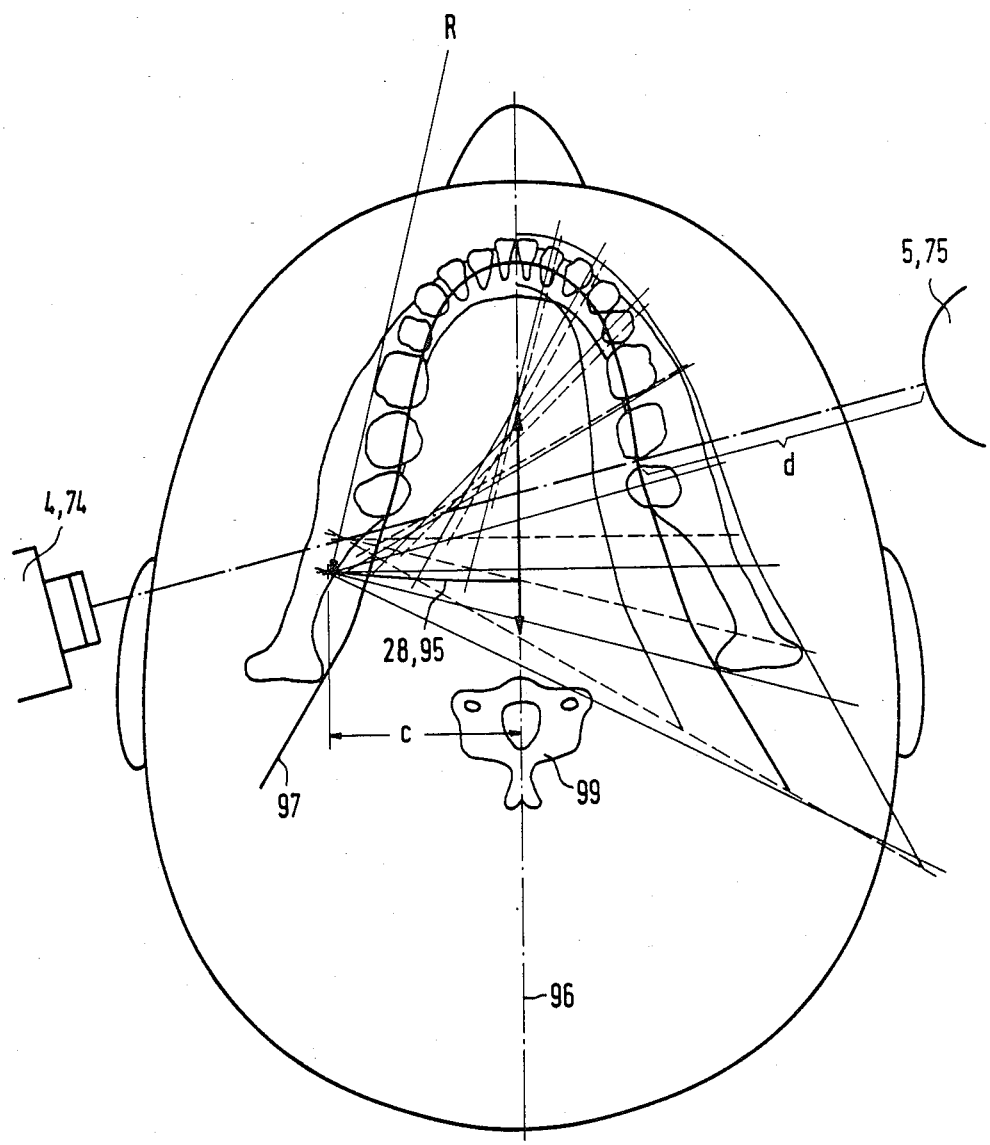
FIG. 14 is a fundamental diagram showing the motions sequence of the device of the present invention in relationship to a patient.

At a center between the two points of articulation 19 and 20 at a distance a, the bearing part 7 contains a swivel axis 25 which is connected to one end of a telescopic arm 26, the other end of the arm being rigidly mounted on the carriage 2. With a uniform drive of both spindle drives 23 and 24, it becomes possible in combination with the above mentioned scissored arm construction to displace the rotary ring 6 parallel to the carriage 2 to vary the spacing b. With a non-uniform adjustment of the two spindle drives 23 and 24, the rotary ring 6 pivots around a swivel axis 25 so that the center 27 of the ring 6 will execute a transverse motion of about ±40 mm on a circle having a radius R of 350 mm. This transverse motion is indicated by the arrow 28 in FIG. 2. In combination with the self-rotational movement of the rotary ring 6 around its center axis 27, the motion sequence which is achieved in the known apparatus by means of the initially cited involved mechanism can be duplicated in a relatively simple way. The swivel axis lies on the symmetry axis of the patient's jaw arch which is to be transilluminated. The swivil radius R is arbitrary in and of itself but given consideration of the selected arrangement of radiation sources and the film cassette holder, the radius is to be established so that the motion sequence relative to the subject as schematically indicated in FIG. 14 will occur.

Figure 3:
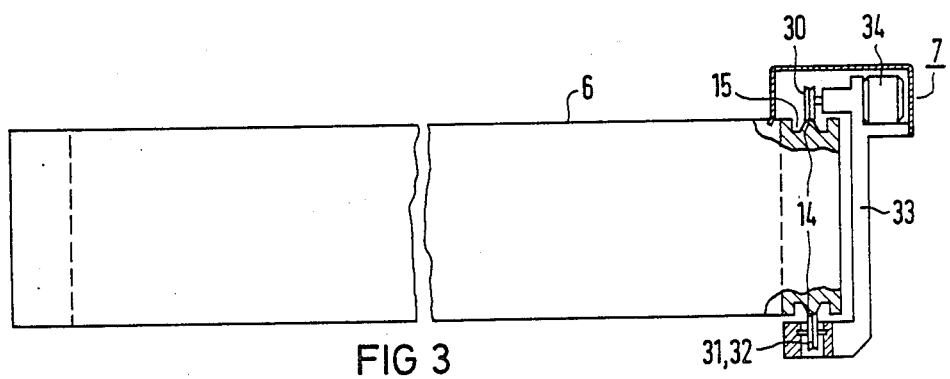
FIG. 3 is a side view of the rotary ring and the bearing support for the ring with portions broken away for purposes of illustration.
Figure 4:
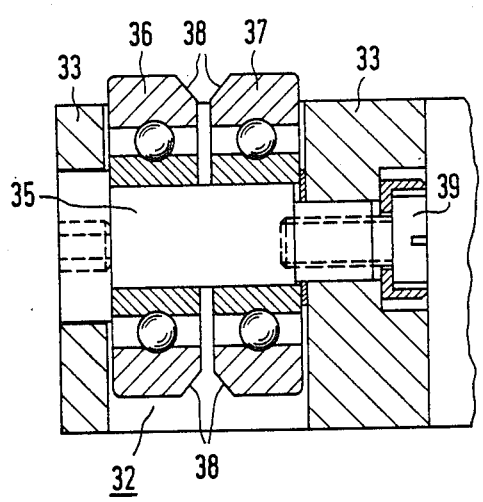
FIG. 4 is a cross-sectional view of a guide roller for the first embodiment.

The bearing part 7 serves first for supporting the rotary ring 6, but also serves to enable the rotary ring 6 to rotate around its center axis 27 as mentioned. This is accomplished by the rotary ring 6 being seated on a guide roller 30 on its upper side and by a pair of guide rollers 31 and 32 on its underneath side. The guide rollers 30, 31, and 32 form a triangular bearing configuration with the roller 30 in the center and the two rollers 31 and 32 on both sides engaging a bottom edge of the ring. For this purpose, the frame 33 of the bearing part 7 is appropriately fashioned with an angle offset as illustrated in FIG. 3. The upper roller 30 is preferably a driven roller, and is coupled to a drive motor 34. The lower two rollers 31 and 32 are only guide rollers, which are for setting the guide play within the triangular bearing support established by the rollers 30 and 32, and their shafts are adjustably arranged in the frame 33. Further details of this structure are illustrated in FIG. 4, which shows the structure of the guide roller 32.

As illustrated, the roller 32 is composed of two ball bearings 36 and 37 which are arranged side-by-side on a common shaft 35. The inner races of these ball bearings 36 and 37 are originally clamped on the shaft 35 and the outer rings or races are freely rotatable relative to one another and have running faces 38 which coact or mate with the running rail 14 of the ring 6. The shaft 35 is an eccentric shaft which is adjustable in the frame 33 in a suitable way, for example, by means of an inside hexagon nut 39 so that the bearing play between the drive rollers 30 and the guide rollers 32 can be set. The rotary ring can also be adjusted relative to the horizontal by means of this eccentric adjustment.

Figure 5:
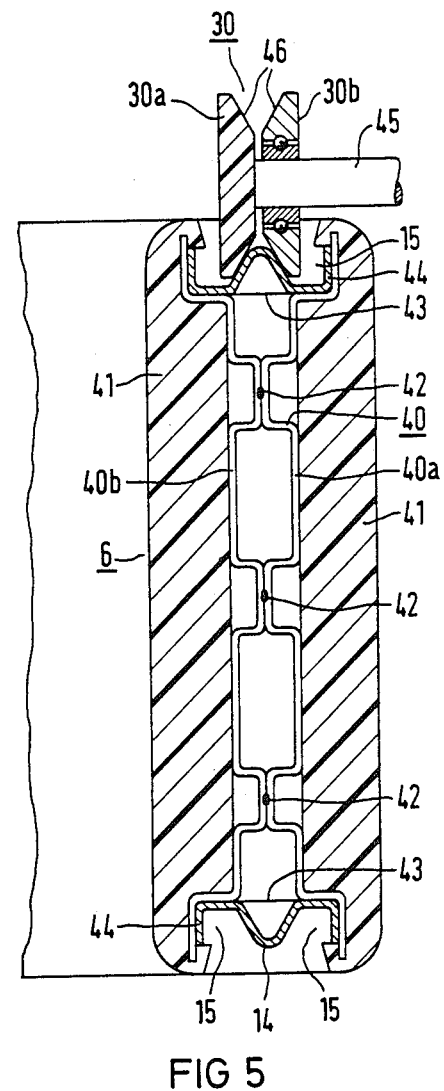
FIG. 5 is a partial cross-sectional view of one modification of the rotary ring in accordance with the present invention.

While the embodiment of the ring 6 in FIG. 3 appeared to be a solid ring having annular ridges 14 to form the track, the ring can be produced by a modification such as illustrated in FIG. 5. In the modification of FIG. 5, the ring is composed of a metal carrier 40 which has an annular shape and on each side has suitable members of cellular or foam material. In the embodiment illustrated, the annular carrier 40 is composed of two halves, 40a and 40b which are respectively sheet metal bands that are welded to one another at locations such as 42. At their upper and lower ends, the halves 40a and 40b form a U-shaped expansion or groove 43 which receives a rolled, annular, profile sheet 44 forming the running annular profile 14. This sheet 44 is welded to the sheets 40a and 40b. As mentioned, the cellular material 41 can be either mounted on the ring 40 or formed thereon.

The drive roller 30 is likewise composed of two halves. The left half 30a is rigidly connected to a drive shaft 45 and a right half, 30b is designed as a ball bearing having an inner ring or race which in turn is rigidly connected to the shaft 45. The outer ring or race, which has the running face such as 46 for engaging the profile 14, is free to rotate on the inner race.

Figure 6:
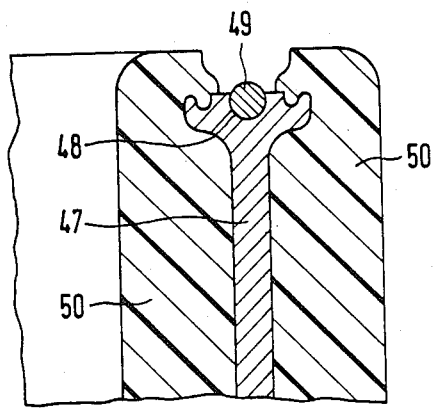
FIG. 6 is a partial cross-sectional view of a second modification of the rotary ring of the first embodiment.

Instead of a construction such as illustrated in FIG. 5, a rotary ring or carrier 47 can have a shape comprising roughly I-shaped member 48 (see FIG. 6). This channel-like member has an annular shape and is provided with a wire ring 49 on each flange for forming the running faces for the running profile 14. In this embodiment, the carrier 47 also has annular members 50 of foam or cellular material on both sides of the member 48.

Figure 7:
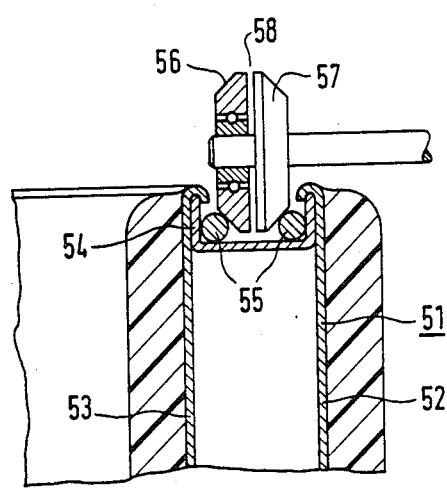
FIG. 7 is a partial cross-sectional view of a third modification of the rotary ring of the first embodiment.

Yet another modification of the rotary ring is illustrated in FIG. 7. In this arrangement, a carrier 51 which has foam annular cellular material secured thereto has a shape of a rectangle and is formed by two spaced annular sheet parts 52 and 53 and a pair of annular, U-shaped channels 54. The sheet parts 52, 53 and channels 54 are welded together to form the box-like configuration. Two wire rings 55 are inserted in the channels 54. In contrast to the previous modifications set forth hereinabove, the rings 55 form two running profiles on which the support and drive rollers such as a drive roller 58 engage. The roller comprises slanted outer sides surfaces 56 and 57, which roll on the profiles 55. For the rest, the drive roller 58 is constructed like the drive roller 30 shown in FIG. 5 in that the surface 57 is on a member rigidly connected to the shaft while the surface 56 is on an outer race of a ball bearing whose inner race is rigidly secured to the shaft. The wire rings can be arranged over the full circumference of the rotary ring, or only over that part of the circumference needed for the adjustment. In the latter case, it is expedient to fix the two ends of the wire rings in a profile sheet 54 by means of clamp parts.

Alternate to the above-mentioned foaming of the carriers, these can also be covered by means of applied profiles of cellular materials.

Figure 8:
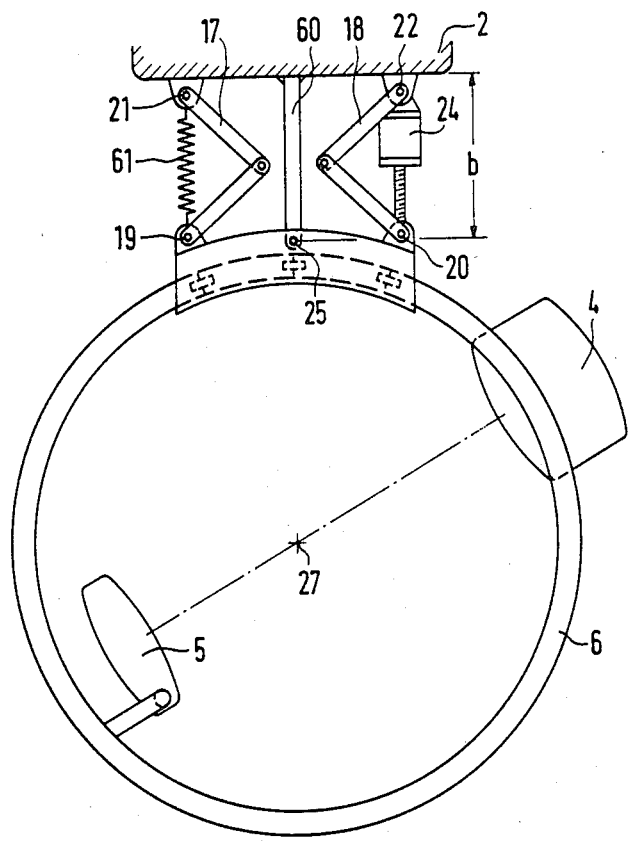
FIG. 8 is a plan view similar to FIG. 2 showing a modification in the adjustment mechanism for the ring of the first embodiment.

An embodiment of the adjustment means is illustrated in FIG. 8 for adjusting the ring 6 relative to the carriage 2. This modification is advantageously provided when it is essentially only standard exposures that are to be produced. Here, the swivelling axis 25 is arranged on a carrier member 60 that is rigidly connected to the carriage 2 so that the distance b remains constant, and is not adjustable. Instead of two spindle drives 23 and 24, as in the modification of FIG. 2, only one drive 24 is provided and a tension spring 61 is provided in place of the second drive. Thus, the spring 61 extends between the pivot connections 19 and 21 as the drive 24 extends between the connections 20 and 22. The tension springs 61 essentially serves the purpose of merely seeing to it that the spindle drive 24 runs essentially free of play.

With this single, or simple, construction, the rotation axis 27 of the ring 6 executes only the above-mentioned transverse motion as indicated by the arrow 28 in FIG. 2, as if the ring rotates around the center axis 27. No adjustment in the longitudinal direction relative to the carriage 2 will occur, and the distance b as mentioned hereinabove from the carriage 2 to the swivel axis 25 remains constant.

Figure 9:
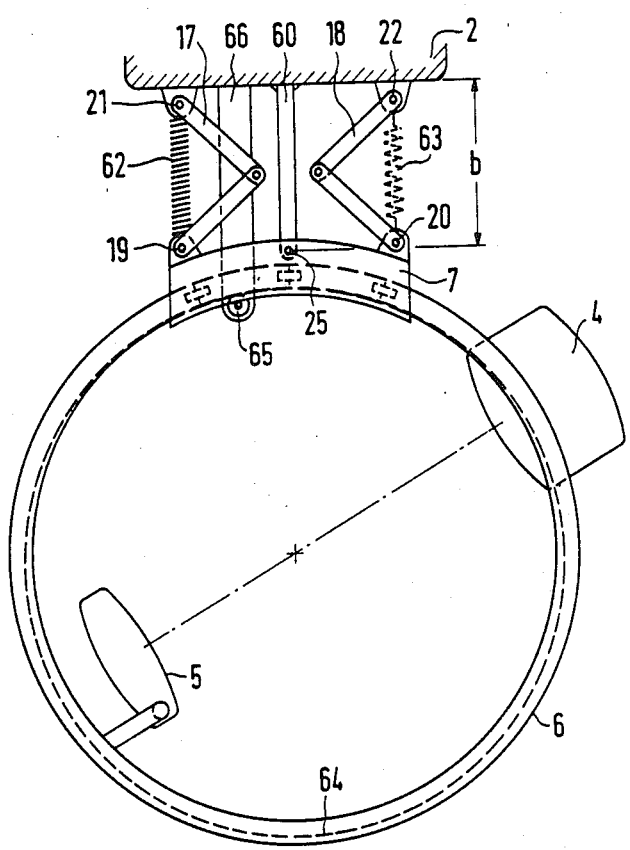
FIG. 9 is a plan view similar to FIG. 2 showing a second modification with regard to the adjustment of the ring.
Figure 10:
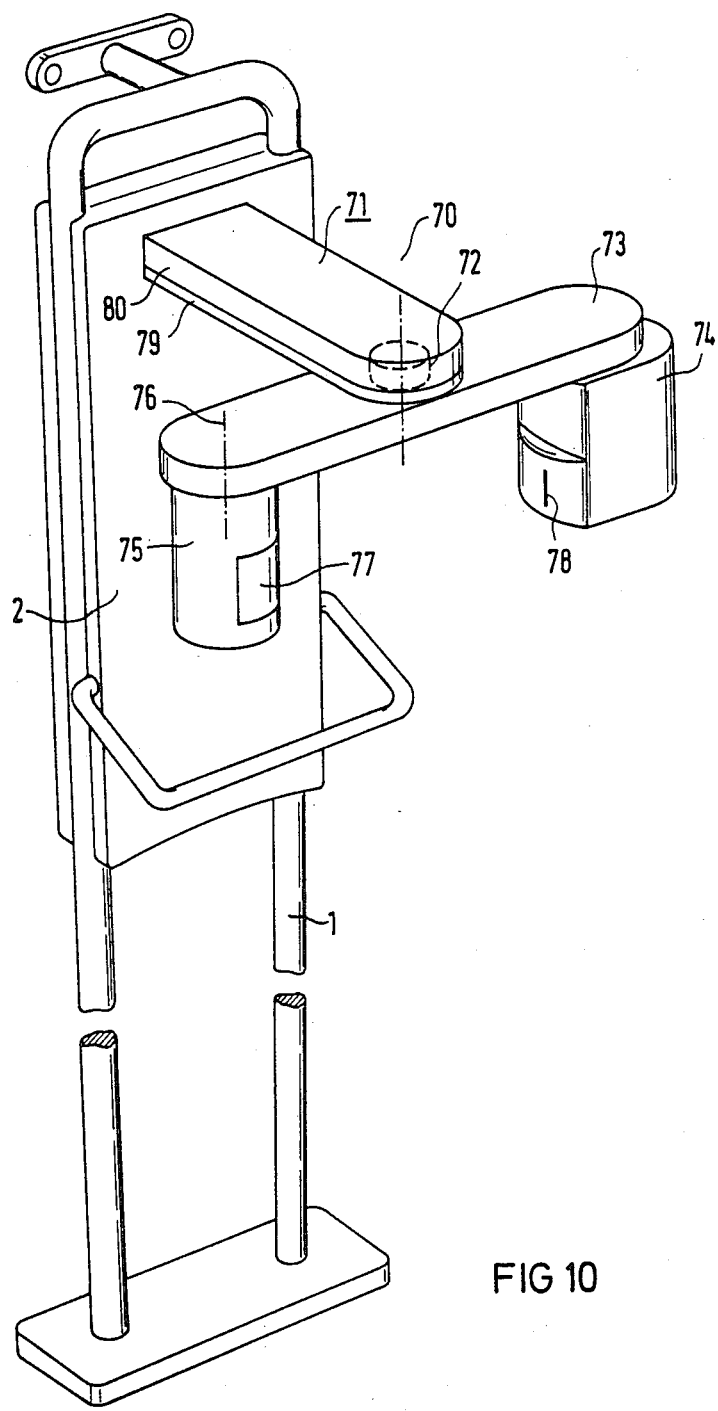
FIG. 10 is a perspective view of a second embodiment of the apparatus according to the present invention.

A third modification of the adjustment means for the swivel axis 25 is illustrated in FIG. 9. Here, the swivel axis 25 is stationarily arranged on a rigid carrier member 60 so that the distance b from the bearing axis to the carriage remains unchanged. A compression spring 62 extends between the pivot connections 19 and 21 while a tension spring 63 extends between the pivot points 20 and 22. The ring 6 on an inside surface contains an eccentric cam curved surface 64 which is pressed against a roller 65 that is fixedly mounted on a carrier 66 that is rigidly secured to the carriage 2. In the arrangement illustrated, the compression spring 62 with the assistance of the tension spring 63 maintains the roller 65 on the surface 64. Since no modification of the distance b is possible, this embodiment or modification likewise is essentially for standard exposures wherein only one slice position is obtained given an immobile patient.

Instead of the curve or cam track 64 which is arranged on the inside of the rotary ring 6, it is also conceivable to provide a correspondingly learning curve on the outside of the ring as well. A guide roller corresponding to the roller 65 will then mate with this external or exterior curve and is supported against the outside of the ring. Instead of a compression spring 62, a tension spring would then have to be provided and a compression spring would have to be placed in the position of the tension spring 63.

Although it is advantageous in terms of production engineering to provide a closed rotary ring, this is nonetheless not absolutely necessary. On the contrary, it is adequate for the ring to be annularly fashioned, covering at least an angular range which corresponds to the orbit curve of the dental arch. Thus, a circumferential angle amounting to approximately 240-270 degrees is only necessary.

In another embodiment illustrated in FIGS. 15 and 16, a closed rotary ring is provided. In this embodiment, the rotary ring 6 is arranged concentrically relative to an annular bearing part 100. In this embodiment, the annular bearing part 100 is held on the carriage 2 by means of the above-described adjustment mechanism as in the case of the bearing part 7 in the embodiment of FIGS. 1 and 2. The rotary ring 6 is seated by means of a plurality of bearing members such as balls or rollers 101 that are arranged in the circumference of the ring and contains a channel 102 in which a flat belt 103 is inserted. This flat belt 103 is an endless belt, and is conducted through a drive roller 104 (FIG. 16) which, together with a drive (not illustrated in detail), is pivotably mounted on the stationary bearing part 100 so that an adequate belt tension is established and avoids slippage between the belt and rotary ring.

A second embodiment of the invention is illustrated in FIGS. 10-13. In this embodiment, the rotary unit 70 is provided instead of the rotary unit 3, which had the rotary ring 6. The rotary unit 70 is composed of a boom 71 which is rigidly arranged on the carriage 2 and rotatably mounts a second boom member or carrier 73 on one end of which the X-ray source 74 is rigidly secured. At the other end of the carrier 73, a film cassette holder 75 is rotatably arranged by means of further axial bearing means 76. By means of the bearing 76, the film cassette indicated at 77 can be moved relative to the radiation source, or respectively, relative to the beam exit opening 78 of the source 74.

Figure 11:
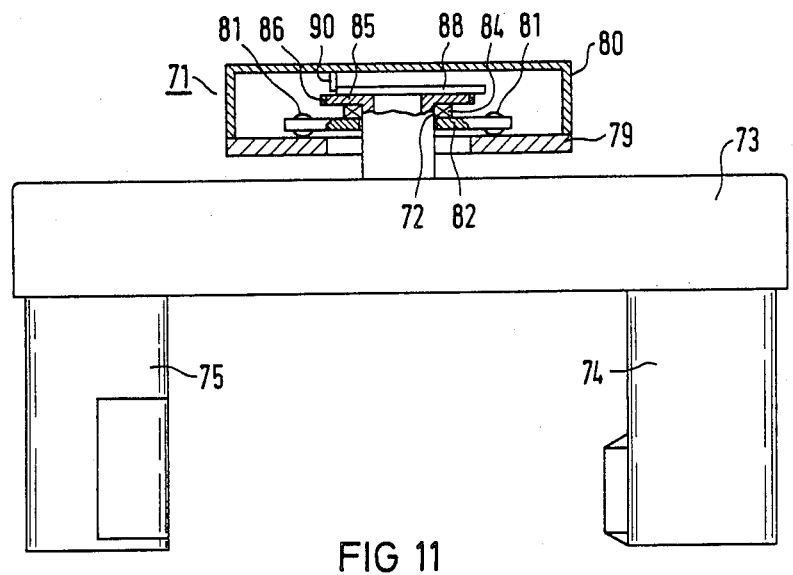
FIG. 11 is a side view of a part of the apparatus of FIG. 10 with portions broken away for purposes of illustration.
Figure 12:
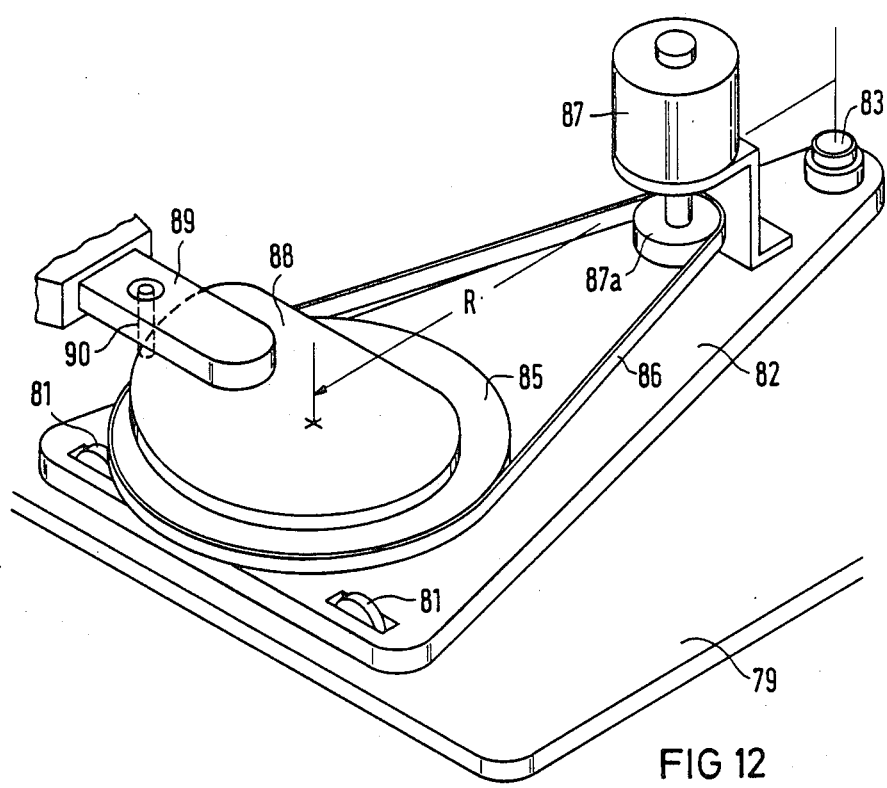
FIG. 12 is a perspective view with portions removed for purposes of illustration of a portion of the device of FIGS. 10 and 11.
Figure 13:
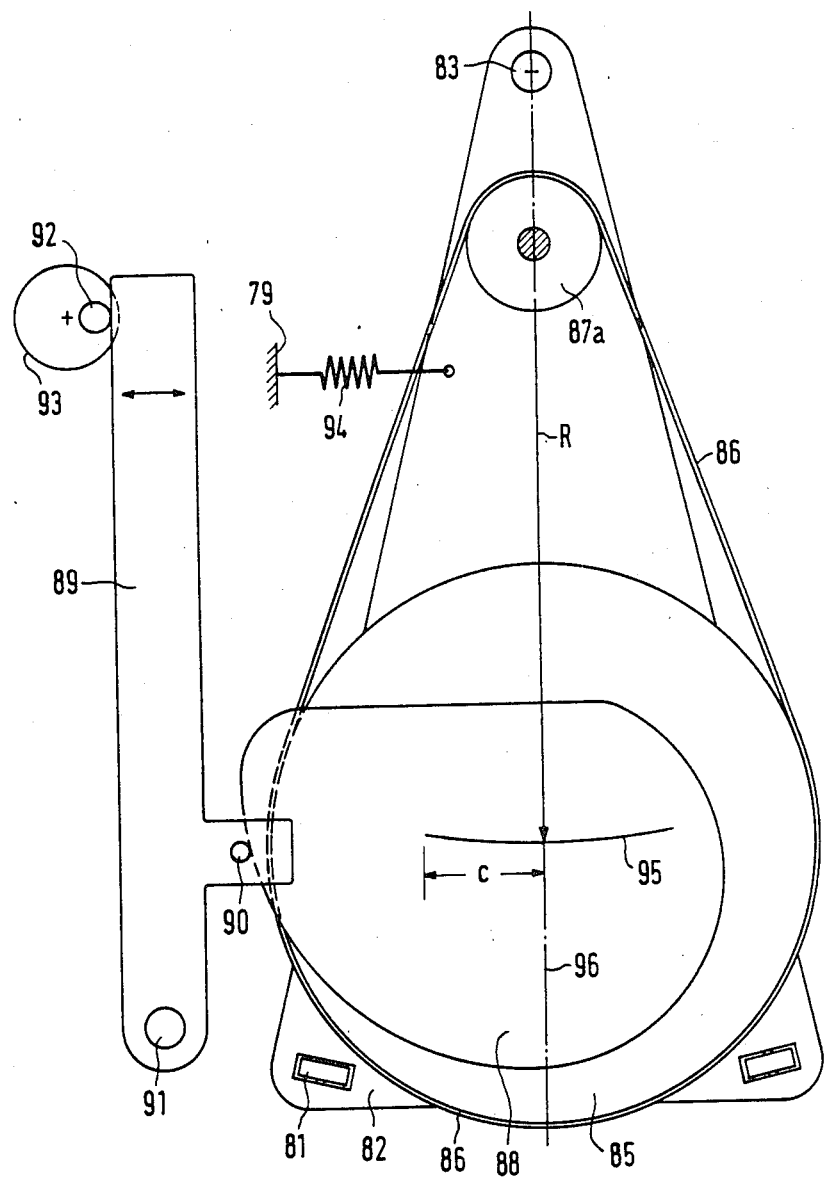
FIG. 13 is a plan view of the arrangement of FIG. 12 schematically illustrating the motions or the operation thereof.

The boom 71 contains a base plate 79 which is rigidly connected to the carriage 2 and the base plate is covered by hood-like covering 80. As is best illustrated in FIG. 11, 12 and 13, the base plate 79 is provided with a pivot bearing 83 having a veritcal axis on which a swivel plate 82 is mounted for movement on the plate 79. To aid in the movement, the plate 82 has rollers such as 81. As may be seen from FIG. 11, a disk 85 is rigidly connected to the axle 72 and, thus, to the carrier 73, which is rotatably seated on the swivel plate 82 by means of a ball bearing 84. The disk 85 receives a drive belt 86 which is connected to a pulley 87a of an electric motor 87. The carrier 73 and the belt sheave 85 thus rotate around a common axis which corresponds to the first axis 27 in FIG. 2 of the previous embodiment.

A cam plate 88 is rigidly mounted on the belt sheave 85 and is engaged by a pin 90 which is mounted for rotation by a ball bearing in a carrier 89 and is pressed against the cam plate 88. As best illustrated in FIG. 13, one end of the carrier 89 is pivotally connected to the base plate 79 by means of a bearing 91 and has its other end engaged against a further pin 92 which is eccentrically arranged on a motor adjustable plate 93. A change of the slice position can thus be achieved for the purpose of an adaptation of the slice enter relationship, for example, given jaw widths deviating from the "normal curve" which are far greater or far smaller. A spring element 94 is provided between the swivel plate 82 and the base plate 79 so that the cam plate 88 is always pressed against the pin 90.

The motion sequence of the carrier of the radiation source and the film cassette holder is composed of two motions. These two motions are a rotary motion, which the carrier executes around the axis 72, and a swivel motion of the swivel plate 82 around the pivot point 83 which swivel motion is transferred to the axis of the axle 72. The rotation axis, which is the axle bearing 72, thus moves on a circular path 95 in FIG. 13 which proceeds at a right angle relative to a symmetrical axis of the symmetry axis 96 of the subject or patient. The swivel radius R and the excursion c are thereby selected so that the optimum perpendicular transillumination direction can always be achieved given a constant distance d (FIG. 14) between the film and subject (the center of the slice).

In accordance with the advantageous execution, the pivot bearing 83 can also be arranged additionally adjustable in the direction of the symmetry axis 96. To this end, the base plate 79 would have to be arranged longitudinally displaceable relative to a further boom secured to the carriage 2. Such an adjustment in the longitudinal direction would occur during rotation and would be optionally controlled either mechanically via a learning or cam curve, or via a separate electrical drive.

With reference to the basic diagram of FIG. 14, the beam course for the right half of the jaw of a patient is illustrated namely with the solid lines for the apparatus of the invention and with broken lines for an apparatus of the prior art. In the illustration, positions 4 and 74 are the radiation source, while positions 5 or 75 are that of the film cassette holder. The motion path of the mechanical pivot point is reference 28, 95, whereas the symmetry axis of the subject is 96 and the slice curve is the solid line 97. The spinal column of a patient is indicated at 99. This may be seen from the drawing as compared to the prior art. The mechanical pivot points of the present invention lie closer to the spinal column whereby a shadow formation produced by the image of the opposite jaw half, which is necessarily smeared per se is noticeably reduced.

Although various minor modifications may be suggested by those adverse in the art, it should be understood that we wish to embody within the scope of the patent granted hereon all such modifications as reasonably and properly come within the scope of our contribution to the art.

We claim as our invention:

1. In a dental X-ray diagnostic apparatus for producing panoramic tomograms of a jaw of a patient, said apparatus including a rotary unit arranged on a carriage of a stand, said rotary unit comprising a carrier rotatable on a first vertical axis, a source of radiation being mounted on the carrier, a holder for a film cassette being adjustably mounted on the carrier diametric to said source so that the radiation coming from the radiation source impinges on said film cassette essentially perpendicular thereto, said rotary unit including an adjustment mechanism by which the carrier is adjusted in an orbital curve corresponding to a dental arch of the patient, the improvements comprising the carriage having a bearing part, said carrier being a closed rotary ring having a center point and being held by the bearing part for rotation around the center point, said film cassette being mounted on said ring for adjustment relative to said source, and said adjustment mechanism containing first adjustment means for rotating said ring on said center point around the first vertical axis and second adjustment means for swivelling the ring around a vertical swivel axis located adjacent a connection of the ring to the bearing part and offset from the first vertical axis by a swivel radius, said swivelling being transverse relative to a symmetry axis of the jaw during a rotational motion around the first axis, an excursion for the swivelling and said swivel radius being selected so that a perpendicular transillumination direction through said jaw is always provided in the movement of the rotary unit to provide a constant distance between the jaw and film.

2. In a dental X-ray diagnostic apparatus according to claim 1, wherein the swivel axis is formed by a pivotal connection between the bearing part and a first arm rigidly mounted on the carriage, said second means including two pairs of scissor arms arranged on each side of said first arm and connected to the carriage and bearing part by pivotal connections and means for pivoting the bearing part on said first arm.

3. In a dental X-ray diagnostic apparatus according to claim 2, wherein said first arm is a telescopic arm and said means for pivoting includes a spindle drive provided for each of the two pairs of scissor arms so that the ring can be pivoted around the swivel axis and the distance of the swivel axis from the carriage can be changed.

4. In a dental X-ray diagnostic apparatus according to claim 2, wherein the first arm is a rigid arm so that the swivel axis is fixed relative to the carriage, and the means for pivoting include a single spindle drive arranged with one of the two pairs of scissor arms and a tension spring arranged with the other of said two pairs.

5. In a dental X-ray diagnostic apparatus according to claim 2, wherein the first arm is a rigid arm so that the swivel axis is fixed relative to the carriage, said means for pivoting including a tension spring coacting with one of the pairs of scissor arms and a compression spring arranged with the other pair, a cam surface eccentrically arranged relative to the center point of said rotary ring, a follower engaging said cam surface to cause swivelling of the ring as the ring is rotated around its center point.

6. In a dental X-ray diagnostic apparatus according to claim 1, wherein the first adjustment means include two spaced guide rollers engaging a lower edge of the ring and one drive roller disposed between the two lower guide rollers and engaging an upper edge of the ring, said ring having a running profile over at least an arc of 240 degrees on each of said upper and lower edges, said running profile being engaged on the upper edge by the drive roller and on the lower edge by said guide rollers.

7. In a dental X-ray diagnostic apparatus according to claim 6, wherein said drive roller is coupled to a drive shaft of a drive motor, said drive roller being composed of two halves forming a running face for engaging the running profile, one of said halves being rigidly secured to the drive shaft and the other of said halves being freely rotatable relative to the drive shaft.

8. In a dental X-ray diagnostic apparatus according to claim 6, wherein each of the guide rollers comprise two ball bearings with inner races being clamped side-by-side on a common shaft, outer races of each said ball bearings being freely rotatable relative to one another and providing running faces for engaging the running profile, a shaft of at least one of said guide rollers being eccentrically mounted to allow adjustment in a horizontal direction.

9. In a dental X-ray diagnostic apparatus according to claim 1, wherein said rotary ring is received in an annular bearing part concentrically arranged relative to said ring.

10. In a dental X-ray diagnostic apparatus according to claim 9, wherein the first means includes a drive belt engaging a periphery of the rotary ring.

11. In a dental X-ray diagnostic apparatus according to claim 1, wherein the rotary ring is formed by an annular member with inner and exterior surfaces, said member having annular cellular shells attached to the inner and exterior surface.

12. In a dental X-ray diagnostic apparatus according to claim 11, wherein the annular member is formed of two halves welded to one another, said two halves being formed of rolled sheets of metal and having upper and lower edges.

13. In a dental X-ray diagnostic apparatus according to claim 12, wherein each of the two halves on the upper and lower edges are formed with a bent profile to form a U-shaped annular groove for receiving a running profile formed of a metal ring inserted therein.

14. In a dental X-ray diagnostic apparatus according to claim 12, wherein each of the two halves are connected to an annular channel-shaped member at each edge, each channel-shaped member having two annular rings secured therein for forming running surfaces for engagement by guide wheels of said first means.

15. In a dental X ray diagnostic apparatus according claim 1, wherein the rotary ring is formed by a single annular channel member having a cross-section of an I-beam with end sections, a ring being inbedded in each of the end sections of said annular channel member for forming a running profile for engagement by guide wheels of the first adjustment means.

16. In a dental X-ray diagnostic apparatus for producing panoramic tomograms of a jaw of a patient, said apparatus including a rotary unit arranged on a carriage of a stand, said rotary unit comprising a carrier rotatable on a first vertical axis, a source of radiation being mounted on the carrier, a holder for a film cassette being adjustably mounted on the carrier diametric to said source so that the radiation coming from the radiation source impinges on said film cassette essentially perpendicular thereto, said rotary unit including an adjustment mechanism by which the carrier is adjusted in an orbital curve corresponding to a dental arch of the patient, the improvements comprising the film cassette being mounted adjustably relative to said radiation source, said carriage having a rigid base plate, and said adjustment mechanism containing first adjustment means for ratating said carrier around the first vertical axis and second adjustment means for swivelling the carrier around a single swivel axis offset from the first axis by a swivel radius and transverse relative to a symmetry axis of a subject during the rotational motion around the first vertical axis, said carrier having an axle mounted for rotation on a swivel plate, said swivel plate being pivotally connected to said base plate at the single swivel axis, the first adjustment means including a rotary drive having a drive sheave connected directly to the axle of the carrier, the second adjustment means comprises means connected to said drive sheave to rotate therewith and pivot the swivel plate around the single swivel axis with excursion for the swivelling and the swivel radius being selected so that a perpendicular transillumination direction through said subject is always provided in the movement of the rotary unit to provide a constant distance between the subject and film.

17. In a dental X-ray diagnostic apparatus according to claim 16, wherein said rotary drive includes a motor secured on the swivel plate, said motor having a pulley with a belt connected to the drive sheave.

18. In a dental X-ray diagnostic apparatus according to claim 17, wherein the means connected to the drive sheave includes a cam plate, and the second adjustment means includes a control cam on said cam plate engaging a follower arranged on the base plate so that as the drive sheave rotates, said axle shifts in said base plate.

19. In a dental X-ray diagnostic apparatus according to claim 18, wherein the follower is adjustably mounted on said base plate.

20. In a dental X-ray diagnostic apparatus for producing panoramic tomograms of a jaw of a patient, said apparatus including a rotary unit arranged on a carriage of a stand, said rotary unit comprising a carrier rotatable on a first vertical axis, a source of radiation being mounted on the carrier, a holder for a film cassette being adjustably mounted on the carrier diametric to said source so that the radiation coming from the radiation source impinges on said film cassette essentially perpendicular thereto, said rotary unit including an adjustment mechanism by which the carrier is adjusted in an orbital curve corresponding to a dental arch of the patient, the improvements comprising the carriage having a bearing part, said carrier being a rotary member having a ring-like shape with a circumferential angle of at least 240°, a center point and being held by the bearing part for rotation around the center point, said film cassette being mounted on said member for adjustment relative to said source, and said adjustment mechanism containing first adjustment means for rotating the member on said center point around the first vertical axis and second adjustment means for swivelling the member around a vertical swivel axis located adjacent a connection of the member to the bearing part and offset from the first vertical axis by a swivel radius, said swivelling being transverse relative to a symmetry axis of the jaw during a rotational motion around the first axis, an excursion for the swivelling and said swivel radius being selected so that a perpendicular transillumination direction through said jaw is always provided in the movement of the rotary unit to provide a constant distance between the jaw and film.

21. In a dental X-ray diagnostic apparatus according to claim 20, wherein the first adjustment means includes two spaced guide rollers engaging a lower edge of the member and one drive roller disposed between the two lower guide rollers and engaging an upper edge of the member, said member having a running profile over at least an arc of 240° on each of said upper and lower edges, said running profile being engaged on the upper edge by the drive roller and on the lower edge by said guide rollers.

* * * * *